United States Patent [19]

Leser

[11] Patent Number: 4,459,487

[45] Date of Patent: Jul. 10, 1984

[54] METHOD AND APPARATUS FOR IDENTIFYING OBJECTS SUCH AS BOTTLES BY SHAPE

[75] Inventor: Jacques Leser, Montpellier, France

[73] Assignee: Supermarket Systems, Saint Lamb ert des Bois, France

[21] Appl. No.: 233,727

[22] Filed: Feb. 12, 1981

[30] Foreign Application Priority Data

Feb. 12, 1980 [FR] France .............................. 80 03073
Aug. 6, 1980 [FR] France .............................. 80 17400

[51] Int. Cl.³ ............................................ G01N 21/86
[52] U.S. Cl. .............................. 250/560; 250/223 B; 356/376; 209/525
[58] Field of Search ................... 250/223 B, 560, 561, 250/578; 356/240, 376, 385, 386, 387, 379, 380–384; 209/525, 529

[56] References Cited

U.S. PATENT DOCUMENTS 4,079,416 3/1978 Faani et al. ........................ 358/106

Primary Examiner—David C. Nelms
Attorney, Agent, or Firm—Pollock, Vande Sande & Priddy

[57] ABSTRACT

An object such as a bottle to be identified by its shape is made to travel between a source and an elongated radiation receiver in a direction oblique relative to the travelling direction of the object so as to define, during the travelling, positions in which said receiver presents a segment, the points of which are at least partly occluded by the object, flanked by first and second segments (X and Z) not occluded. The length variations of at least two of the three segments of said receiver are read out for obtaining a characteristic relation of the object shape. Parameters of this relation are compared with corresponding parameters of characteristic relations of the shape of typical objects so as to find out whether the object travelling belongs to the category of one of the typical objects, and if in the affirmative, to which of them. The invention is applicable to the automating refund of deposits on bottles.

27 Claims, 10 Drawing Figures

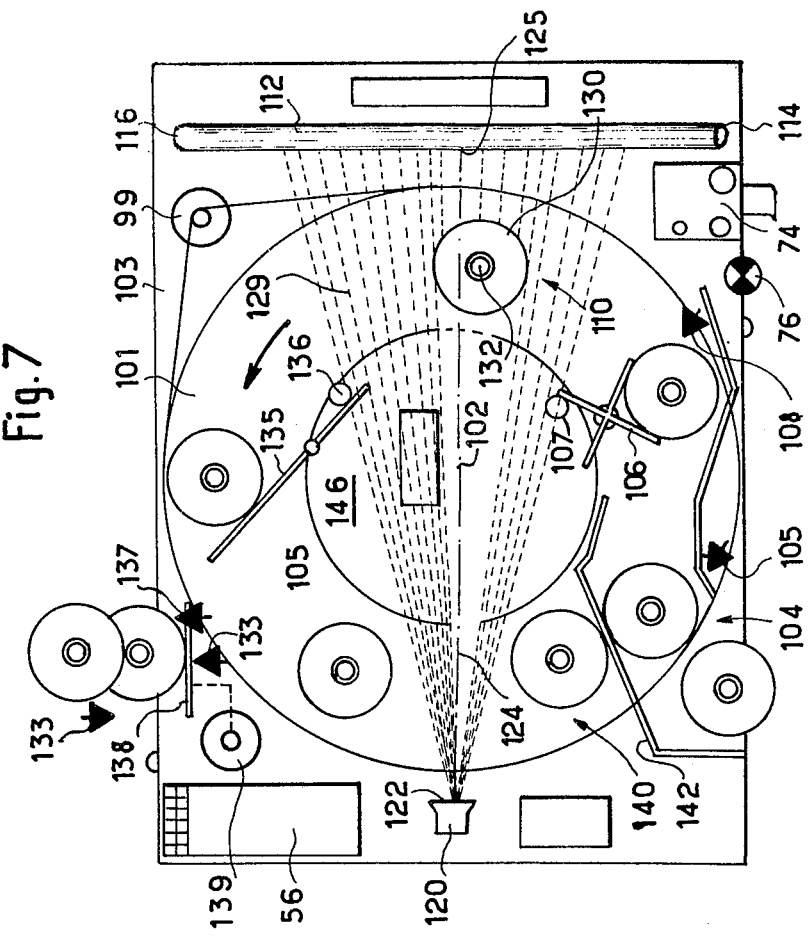
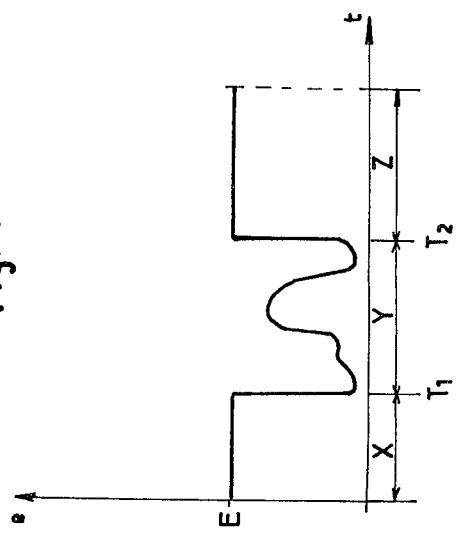

Fig. 10

METHOD AND APPARATUS FOR IDENTIFYING OBJECTS SUCH AS BOTTLES BY SHAPE

FIELD OF THE INVENTION

The present invention relates to the identification of objects such as bottles, as a function of their shape.

In retail trades of liquids, and particularly of beverages or drinks, the glass bottles are either non-returnable containers and not used again, or returnable containers subject to a deposit which is the object of a refund to the customer when he brings the bottles back to the merchant.

The necessity has been felt, in so-called "large surface" stores where a large number of bottles are sold and brought back, to automate the identification of the bottles. This is the reason why apparatuses have been proposed which carry out said function and allow the delivery of a ticket representative of the bottle value, or deposit, and sort out the returnable bottles which are to be re-used from the non-returnable bottles which are to be destroyed.

BACKGROUND OF THE INVENTION

In a known apparatus, the bottles are placed on a conveyor and they occlude the beam of light transmitted by a source transverse to the path of travel of the conveyor and directed towards an assembly of detectors. Means are provided for determining one or several dimensions of the bottles as a function of the condition, (degree of illumination attenuation) of said detectors. Control means allow displacing the beam of light so that each detector is successively reached. The identification is then obtained through a comparison between said measured dimension or dimensions and one or several corresponding dimensions stored in a memory. In order that the measurement be accurate, the scanning movement of the beam of light is synchronized with that of the conveyor. The scanning and synchronizing means make the construction of the apparatus complex.

OBJECTS AND SUMMARY OF THE INVENTION

The method and apparatus according to the invention allow identifying objects such as bottles, independently of their speed of travel.

According to the method, the objects to be identified are made to travel between a radiation source and a receiver, so as to vary the quantity of radiation received by the receiver as a function of the profile of said objects. Said method is characterized in that the useful portion of the receiver is elongated in a direction oblique relative to the travelling direction of the objects, so that, during the travelling movement, there is a segment of the receiver which is at least partly occluded by the object, and first and second segments which are not occluded, on either side of said occluded segment, the corresponding length variations of at least two of said three segments being read out in order to obtain a relation characteristic of the object shape.

When the object travels between the source and the receiver, the length of each of the three segments thus defined varies since the object shuts out a fraction of the radiation incident on the receiver which depends on its shape. The respective relations between the successively read out values of such lengths are characteristic of said shape. They are independent of the object speed.

More precisely, to each position of an object of predetermined shape corresponds a ratio between the lengths of at least two of the three defined segments, which depends on said position and on said shape. Thus, the length variation of one of said segments as a function of that of another of said segments when the object is travelling is independent of time and therefore of the speed of the movement of the objects to identify. The relation obtained depends only on the object shape and dimensions.

In order to take advantage of said characteristic relation of the object in movement, it is compared with a series of known and established relations corresponding to the shapes of typical objects, in order to determine whether the object belongs to one of said types.

Preferably, one reads out the lengths of the first and second segments for obtaining a relation between them when an object is moving. In particular, when the method is applied to objects having a narrowed shape in a transverse direction relative to the travelling direction, such as bottles, one of the segments, such as the first segment of the receiver, is substantially less inclined relative to the perpendicular to one of the narrowed profile sides upon which it bears than is the second segment relative to the perpendicular to the opposite side, and it is preferably the length variation of the second segment as a function of that of the first which is determined.

Indeed, when the first segment is limited by said narrowed portion of the object profile, its length has a tendency to increase or to diminish in a uniform and relatively regular manner during the travel of the object due to the fact that the inclination of said first segment relative to the perpendicular to said profile remains relatively small. One can take advantage of this recognized fact for reading out the length variations of the first segment in the form of quantified values for forming a uniform progression of successive values, increasing or decreasing, and, for each value thus read out of the first segment length, one determines the corresponding value of the second segment length. This method may be advantageously carried out by addressing the second segment length measurements in memory positions determined by the successively read out values of the first segment length.

According to a preferred embodiment, the elongated receiver is placed in a position and the objects are made to travel relative to said receiver in a direction such that, for at least one set of determined objects, during this travelling, each object penetrates the radiation incident on said receiver by occluding an area situated between the ends of the latter. This mode of operation has the advantage that, as soon as the object to be identified penetrates the radiation area, two corresponding length values of the first and second segments are available. Moreover, according to a particularly useful feature in practice, it is then possible to determine the length of each of the first and second segments from the moment the object penetrates said radiation, by examining the illumination level of each of the first and second segments by starting from the corresponding end of the receiver and by progressing towards the opposite end of the latter until a transition area of the illumination level is met, and which is then considered as safely corresponding to one of the profile edges of the object to be identified. Indeed, when transparent bodies such as bottles are involved, the occluding of the receiver by the object is not always total, particularly in the central portion of the bottle. But in the vicinity of the bottle edges the thickness of the glass through which the light travels increases and there is a relevant absorption of the light. The transition between the first or second segment and the area occluded by the bottle edge is therefore very unequivocal even when the central portion of said area may receive a substantial illumination.

According to an embodiment, the receiver is made of discrete elements and the length of each of said first and second segments is determined by counting the number of discrete elements receiving the radiation without interception by the object by starting from the respective receiver end.

An object of the invention is also an identification machine for objects such as bottles, of the type comprising a conveyor, a receiver sensitive to radiation intercepted by objects travelling on the conveyor, characterized in that said receiver is elongated obliquely relative to the travelling direction of the conveyor, so that, during the movement of each object, a segment occluded by said object, flanked by first and second segments which are not occluded, the machine further having means for reading out the length of at least two of said three segments of variable length when the bottle travels past the receiver.

For a machine built for returning the deposit payed on bottles, the conveyor comprises a horizontal platform on which the bottles may be placed with the axis vertical.

Preferably, taking in account the maximum dimension of the objects to be identified, the receiver is placed so that one of its ends is never occluded by said object if it is part of a set of predetermined objects to be recognized.

Moreover, the direction of the conveyor movement is then preferably chosen so as to allow the occlusion of an intermediate region of the receiver by each object at the moment it penetrates the radiation incident on said receiver.

According to an embodiment, the machine is comprised of threshold detection means adapted for detecting the illumination level of the receiver points in relation with a threshold, and examination means of the first and second segments from the corresponding end of the receiver towards the opposite end.

According to an embodiment, the machine comprises means for reading out the length of each of the first and second segments by storing digital values corresponding to the lengths of the detected segments.

According to an embodiment, the conveyor is a horizontal transporting device with a loop-shaped path for objects such as bottles, and the receiver is placed at a level which is higher than the tallest of the bottles accepted by the machine.

BRIEF DESCRIPTION OF THE DRAWINGS

The following description is given by way of example, reference being made to the accompanying drawings wherein:

FIG. 4 is a graph illustrating the illumination variations of the elongated receiver resulting from the transparency of the object to be identified, FIG. 7 is a schematic view of a machine to return the deposits on bottles, using the principles of the invention, FIG. 10 is a schematic view of a memory page.

DETAILED DESCRIPTION OF THE EMBODIMENTS

Figure 1:
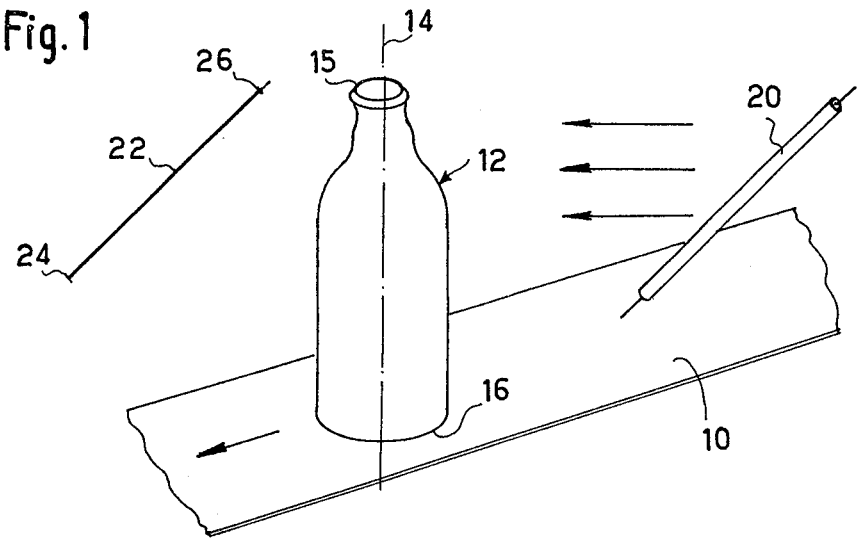
FIG. 1 is a schematic perspective view of a bottle travelling between a source and a receiver in a machine according to the invention.

A machine for returning the deposits on bottles (FIG. 1) comprises a platform of a horizontal conveyor 10 adapted for travelling in the direction of arrow F and for receiving bottles 12 with their axis 14 vertical, the bottom 16 of which is placed on said platform 10. On either side of the space area through which the bottle 12 travels, when carried by the conveyor, are placed, on the one hand, a light source 20, and on the other hand a rectilinear elongated receiver 22 adapted for being illuminated by the light rays emitted by source 20 over all its length when no object such as a bottle 12 intercepts, as least partly, said rays. The source 20 and the receiver 22 are parallel and inclined by about 45° in the travelling direction F of conveyor 10 and in a plane which is parallel to the bottle axis 14 and to the direction F.

The source 20 is constituted, for example, with the assistance of an industrial white elongated fluorescent tube, of small diameter and about 90 millimeters long. It is supplied with a sufficiently high frequency (over 20 KHz) for producing a continuous illumination. An optical system, not shown in FIG. 1, is provided at the inlet of receiver 22 for forming an image of the segments 20 of the source which are not occluded by the bottle on the sensitive surface of receiver 22. The elongated receiver 22 is comprised, for example, of a bar 6.5 millimeters long, comprising 256 photodiodes equally spaced between the ends 24 and 26 of said receiver, each photodiode being 25 micrometers long.

The relative arrangement of the source 20 and of the receiver 22 is such that part of the radiation from source 20 which is incident on receiver 22 is intercepted by bottle travelling on conveyor 10, and in such manner that, during part of this movement, one may define on receiver 22 at least three areas or segments of different illumination: a segment at least partly occluded by the bottle 12 which intercepts part of the radiation incident on said segment, and first and second segments not occluded on either side of the occluded segment, including respectively the ends 24 and 26. Guide means, not shown, allow fixing the distance between the bottle and the receiver 22, with a tolerance of about 1 centimeter, so that, for a given bottle type, the illumination transition on the receiver corresponding to the image of an edge of said bottle remains within a distance corresponding to ±1 photodiode relative to a given means position, whatever the bottle specimen of the type in consideration which is placed on the conveyor.

During the travelling of bottle 12 on conveyor 10 (FIG. 2), the successive relative positions of the receiver 22 which is illustrated by an oblique line and of said bottle 12 move between a position $P_1$ in which the bottle has still not penetrated the radiation incident on the receiver, and a position $P_n$ in which the bottle has passed the space between source 20 and receiver 22. In an intermediate position $P_i$, the bottle intercepts part of the radiation from source 20 and defines the occluded segment of length Y along which the light incident on the receiver is totally or partly absorbed, according to the transparency of the bottle. On either side of said segment, the first segment, of variable length X at the upper portion of the receiver 22, and the second segment of length Z at the lower portion of the segment of receiver 22 receive both the totality of the radiation normally intended for them.

During its travelling, the bottle sweeps (FIG. 2) a parallel space band having a width equal to its height H. The receiver 22 intercepts said band over all its height between the conveyor 10 and intercepts in particular the line corresponding to the path of travel of the bottle top 15. The span of said receiver 22 is such that it intercepts the upper edge of all the bands described by the bottles intended to be recognized by the machine. The upper end 26 of receiver 22 is at a distance M from platform 10 which is greater than the maximum height of said bottles and is never occluded, even by the tallest of said bottles. On the contrary, the lower end 24 can be placed slightly above plane 10, but sufficiently close for allowing the identification of the smallest bottles for which a deposit is to be returned.

When the bottle 12 moves in the direction of arrow F relative to receiver 22, it penetrates the radiation reaching said receiver in the relative position $P_2$. In said position, the left hand side edge $15_1$ of the bottle top 15, or frontal edge if one considers the progress direction of arrow F, intercepts receiver 22 at one point. It is possible to read out a segment of length $X_2$ and a segment of length $Z_2$, the sum of said lengths being equal to the length of receiver 22, the length $Y_2$ being zero.

When the bottle progresses and reaches for instance position $P_3$, the receiver 22 intercepts the horizontal portion of the bottle end 15, the length $X_3$ is equal to $X_2$, while the length $Y_3$ is no more zero and $Z_3$ is smaller than $Z_2$. When the end $15_2$ of the neck 15 of the bottle has passed detector 22, the value of segment X (for example $X_4$ for the relative position $P_4$ of the bottle and the detector) increases progressively as the movement of the bottle on conveyor 10 goes on. The length Z tends to zero starting from position $P_f$ where the bottle meets the end 24 of receiver 22.

For allowing the identification of the bottles, the successive values taken by the lengths of segments X and Z are read out and recorded with a view to exploiting them.

Figure 5:
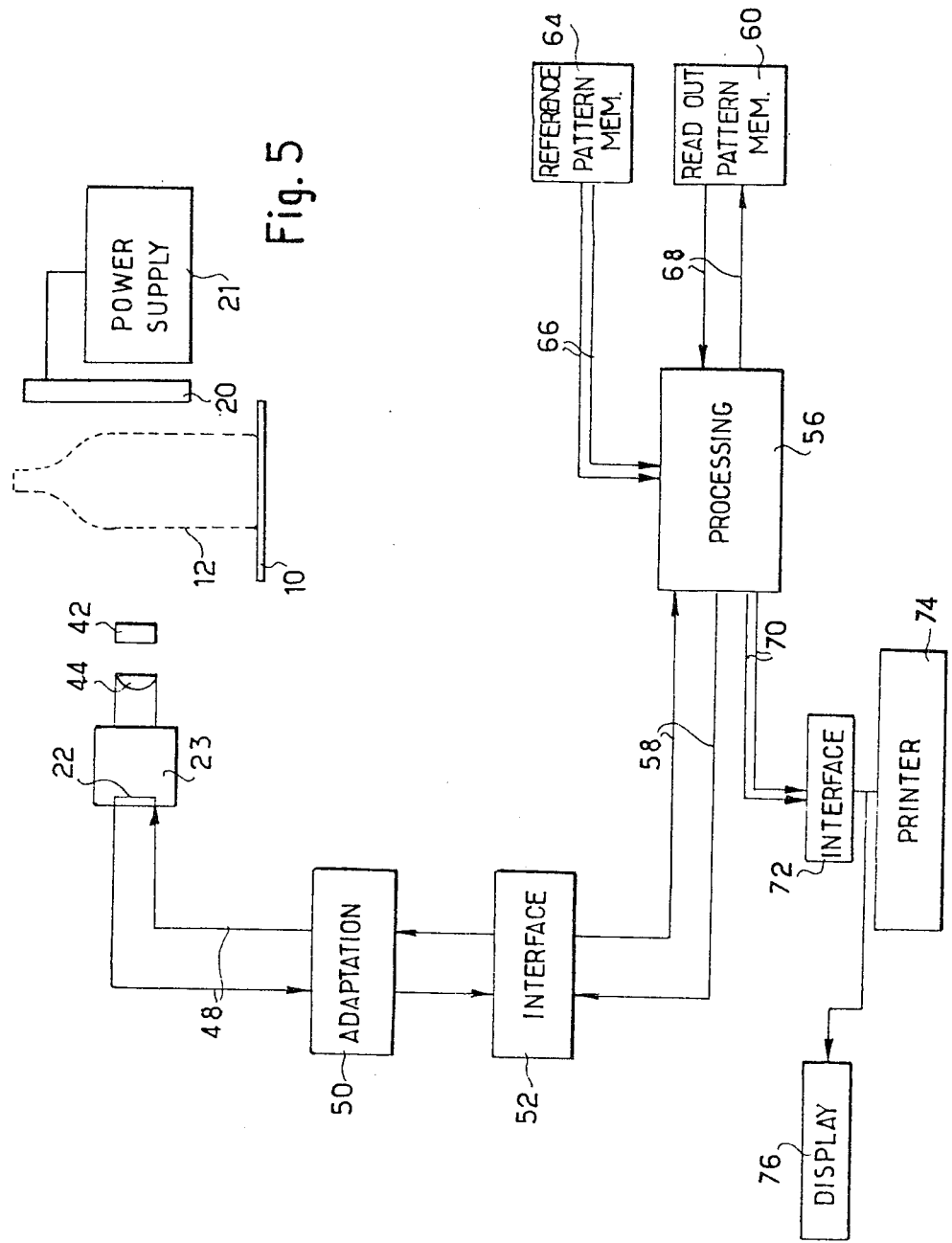
FIG. 5 shows schematically a control circuit for a machine to return the deposits on bottles, according to the invention.

FIG. 5 shows schematically an identification machine equipped with such read-out device. The bottle 12 which is placed on the platform of conveyor 10 travels perpendicularly to the plane of the figure past the inclined fluorescent tube 20 which is supplied with a high frequency voltage by a power supply 21. The bottle 12 is at a distance of about 10 centimeters of said tube 20. It should not be too close to the latter so as not to generate a too important light diffusion in the vicinity of its edges.

Opposite tube 20 relative to the path of travel of the bottle is mounted a casing 23 at the bottom of which is placed the bar 22. An objective lens 44 is mounted in an opening in front of casing 23 for forming an image of the light source 20 such as it is when occluded by the bottle 12 on the bar of photodiodes 22. A polarizing filter 42 mounted in front of the lens is provided for limiting possible reflections on the bottle glass. The lens 44, in this example, has a focal length of 8.5 millimeters and an aperture of F=2. Of course, for carrying out the invention, it is not necessary that bar 22 be in a vertical plane parallel to the bottle axis. In particular, the optical system forming the image of source 20 on the bar could carry out a change of angle, for instance with the assistance of mirrors, or simply the optical axis of lens 44 could be inclined relative to the plane of platform 10 for reasons which will appear later. It is important that the useful portion of the receiver, such as 22, is inclined relative to the travelling direction of the bottle cast shadow on the receiver.

The bar 22 is connected via a bidirectional connection 48 to an adaptation circuit 50 which shapes the series output pulses of bar 22 successively corresponding to the illumination levels of each of the photosensitive elements and transmits a series binary signal to a processing or management circuit 56 via a bidirectional connection 58 through an interface 50. After analysis of the series signal by the processing circuit 56, the X and Z length information is transferred into a read-out pattern memory 60 via a bidirectional connection 68. Said memory 60 is a random access memory (RAM), addressable by the processing unit 56.

The processing circuit 56 made of a microprocessor for example, is adapted for carrying out a comparison of the data stored in memory 60 with typical information corresponding to a predetermined set of bottles and stored in a reference pattern memory 64 connected to this processing unit through a connection 66. The results of the data comparison in memories 60 and 64 lead to a decision of rejection or acceptance of each bottle having passed the space between the source 20 and the receiver 22. This decision is transmitted by a line 70, through an interface circuit 72, to a ticket printer 74 indicating, as the case may be, that the bottle can be accepted by the store and showing the amount of the deposit for which the bottle can be taken back. If the bottle is rejected, this information is shown on a display device 76 informing the customer to take his bottle back.

During the movement of a bottle, the identification procedure is carried out in two successive steps for the acquisition of the measurements of segments X and Z on the one hand, and for an analysis of the measured values for the recognition as such on the other hand.

Explanations will now be given on the acquisition procedure.

In this example, bar 22 is an integrated photodiode network of the type currently and commercially available and described for example in a paper entitled "Les Premiers Réseaux IntégrAUC/e/ s De Photodiodes Et Leurs Applic&tions" by J. Laser published in the EMI magazine, issue no. 166 of Jan. 15, 1973. Such networks are also manufactured by the Reticon Corp. 910 Benicia Ave, Sunnyvale, Calif. 94086 U.S.A., under reference "G-Series Solid State Line Scanners".

Figure 8:
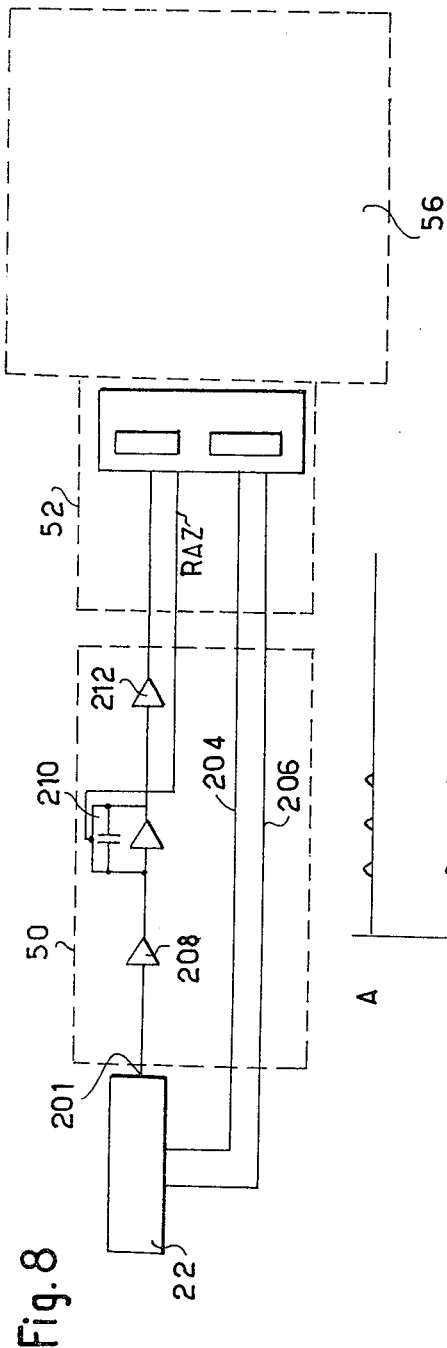
FIG. 8 is a more detailed schematic view of a part of the circuits of FIG. 5.
Figure 9:
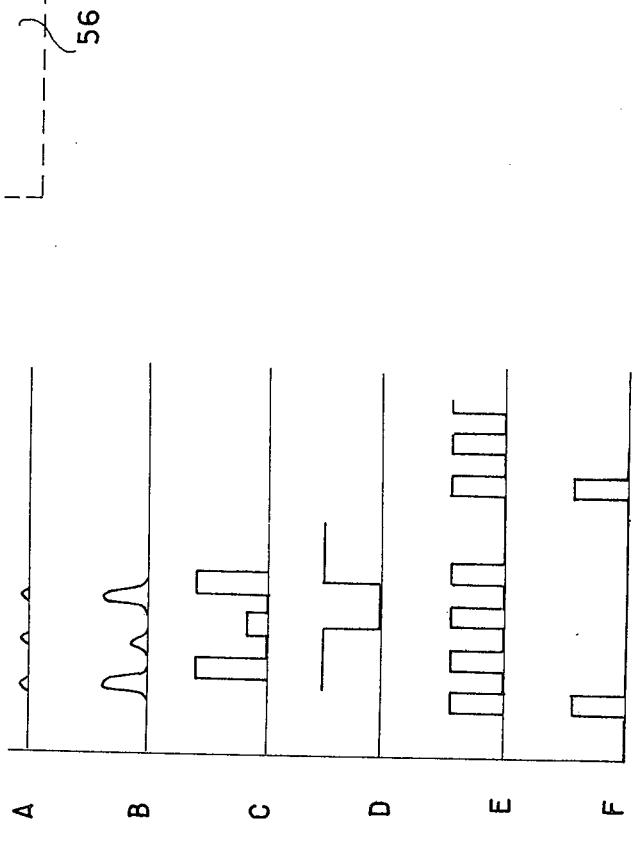
FIG. 9 is a diagram of the signals used in the circuit of FIG. 8.

In such devices, each photodiode is associated with a capacitor integrated in the silicon and a shift register, also integrated, recharges sequentially said capacitors. The more the photodiode illumination, the stronger the capacitor discharged and the more the recharge current is increases. The recharge current pulses (FIG. 9A) appear at output 201 of bar 22 (FIG. 8) under the control of a clock signal CK (FIG. 9E) arriving from the processing unit 56 via a line 204 controlling the self-scanning of the 256 diodes. This self-scanning is repeated 800 times per second under the control of signal ST (FIG. 9F) transmitted from the processing unit 56 via a line 206 to bar 22.

The output pulses 201 of the bar are, in adaptation circuit 50, amplified by an amplifier 208, shaped by an integrator 210 and transmitted to threshold detector 212 which delivers a signal at two levels (FIG. 9D) the transitions of which are in correspondence with the clock pulses CK (FIG. 9E) at the memory of the processing unit 56 through the interface 52.

Figure 10:
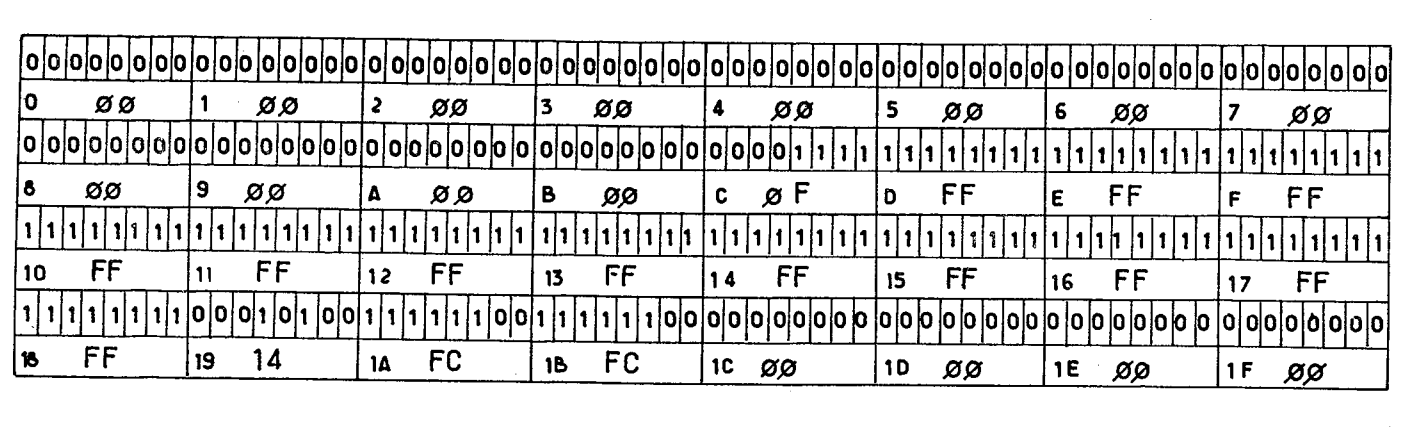

The signals ST and CK are transmitted during the period when the processing unit is in an expectation condition before a bottle intercepts the radiation. As soon as one diode at least is occluded, the signals from each scanning (FIG. 9D) which are 256 in number are stored in 32 fields of a RAM memory, of the processing unit, each level of the input signal corresponding to a 0 or 1 bit. An example of a memory "page" containing said 32 fields is shown in FIG. 10.

The reading of the values of X and Z is carried out by the processing unit which examines the fields sequentially by starting by the extreme field IF until it reaches a field having a content which is not zero, here IB. The processing unit examines then field IB for determining whether it possesses two zero bits, the length of X corresponding to $4 \times 8 + 2 = 34$ photodiodes. (The zero levels in the example shown corresponds to illuminated diodes).

The processing unit carries on in the same manner from the other end of the page, viz. from field O for determining that Z: $12 \times 8 + 4 = 100$. Then, the processing unit examines the fields between C and IB for determining whether the content of one of them is different from FF (8 bits of level 1), which corresponds to a transparency of the bottle. A transparency register is then incremented by one point. At the same time, the X and Z value thus determined are recorded in the read out pattern memory 60 by placing the value determined for Z in a position of said memory the address of which corresponds to the value determined for X. If a value of Z had already been recorded in this position, it is superseded by the new value.

Thus, when a bottle such as 12 intercepts the rays incident on the elongated receiver 22, couples of successive value X and Z are stored in memory 60, the corresponding relation being characteristic of the shape of said bottle. It has been found that, for bottles having different profiles, one obtained different relations between said segment lengths. It is therefore possible to identify a bottle of known shape by comparing the relation obtained by the read-out of the lengths corresponding to the passage of said bottle between the source and the detector and typical relations or patterns already stored corresponding to the known bottles.

The relation between two of the three segment lengths X, Y and Z depends, for a given bottle shape, on the inclination of receiver 22 relative to the travelling direction of the cast shadow of the bottles on said receiver. It has been found that an inclination of about 45°, possibly slightly less, gave favourable results for objects having the shape of bottles. This obliqueness of receiver 22 in the travelling direction of the objects is an essential characteristic of the carrying out of the invention without which no characteristic relation of the shape of said objects could be found between the lengths of two of the segments of receiver 22. This relation does not depend on the travelling speed of the object to be identified, if abstraction is made of the possible operation time of the read-out and analyzing device (FIG. 5).

To each position of the bottle in front of the source corresponds a relation between the lengths of segments X and Z which depends only on said position and on the shape of the bottle. The length variation of one of said segments Z as a function of that of the other segment X, is independent of time and therefore of the speed. Even if the bottle moved back and then moved forward again, the measurements read out would remain in principle the same for a given bottle.

Thus, in order that the acquisition of the measurements be carried out efficiently, it is enough that the bottle starts from one starting point and reaches an arrival point by passing through the radiation independently of its movement between said two points.

The value couples (FIG. 2) $X_2, Z_2; X_3, Z_3; X_4, Z_4; X_i, Z_i$, etc., depend on the shape of the bottle. They depend notably on the height H of said bottle and on the lengths $Y_3, Y_4, Y_i$ of the variable segment of the receiver which is occluded by said bottle.

Figure 3:
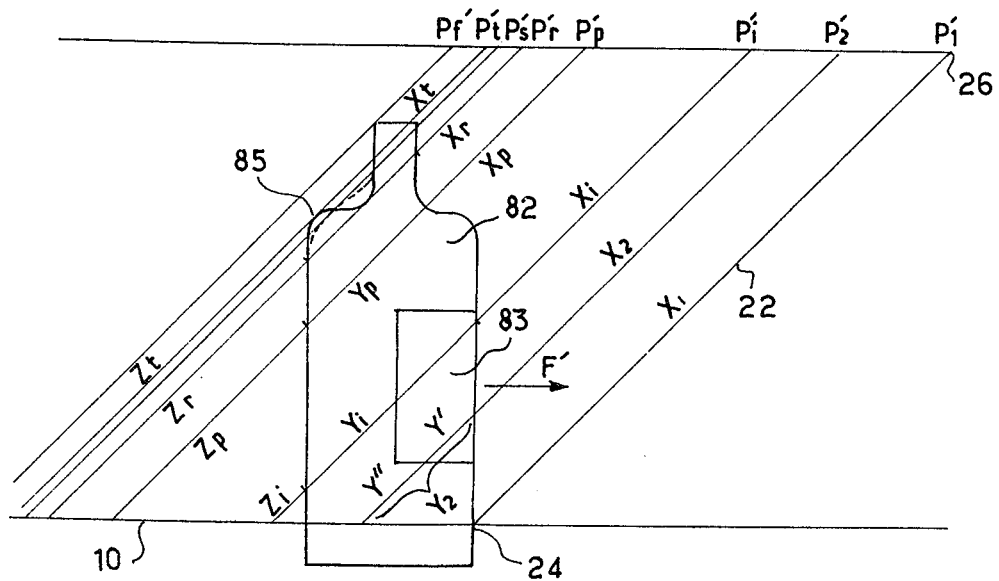
FIG. 3 is a similar view to that of FIG. 2, illustrating some particular application cases of the invention.

In the case of transparent objects such as bottles, one prefers reading out the joint radiations of X and Z, the degree of illumination (or occlusion) of the segment Y being not uniform, and it is desirable to be able to determine as soon as the bottle 12 begins penetrating the radiation between source 30 and receiver 22, a value X and a value Z. In FIG. 3, it has been assumed that the movement of a bottle 82 was in the reverse direction, shown by arrow F', to that of bottle 12 of FIG. 2. The relative positions $P'_1, P'_i, P'_p, \ldots P'_f$ of receiver 22 have been illustrated relative to bottle 82 as it moves along, and in this order. The inclination of the elongated receiver 22 is such that, when the bottle moves in the direction F', it begins intercepting the receiver at a point situated at its lower portion. When the travelling movement goes on, the interception point of the receiver by the bottle moves upward along said receiver, contrary to what would happen in the case of FIG. 2 where the point of attack of the receiver 22 by the profile or the cast shadow of the bottle moves downward, viz. towards conveyor 10. When the bottle reaches the relative position $P'_2$ in which the point of attack of the bottle 82 on receiver 22 corresponds to the base of a label 83 on said bottle, segment $X_2$ is well defined by a line of the receiver the radiation of which is absolutely not intercepted. On the contrary, the degree of occlusion of the corresponding segment $Y_2$ is variable. It is made on the one hand of a portion Y' completely occluded by label 83, and of a portion Y'' receiving light rays which have been able to cross the center of the bottle, in as far as the latter is relatively transparent. If one proceeded without precautions, it would therefore not be impossible that the detection and analysis device of receiver 22 would confuse the area Y'' with a segment of Z type previously defined while the end 24 of the receiver is still occluded.

Figure 2:
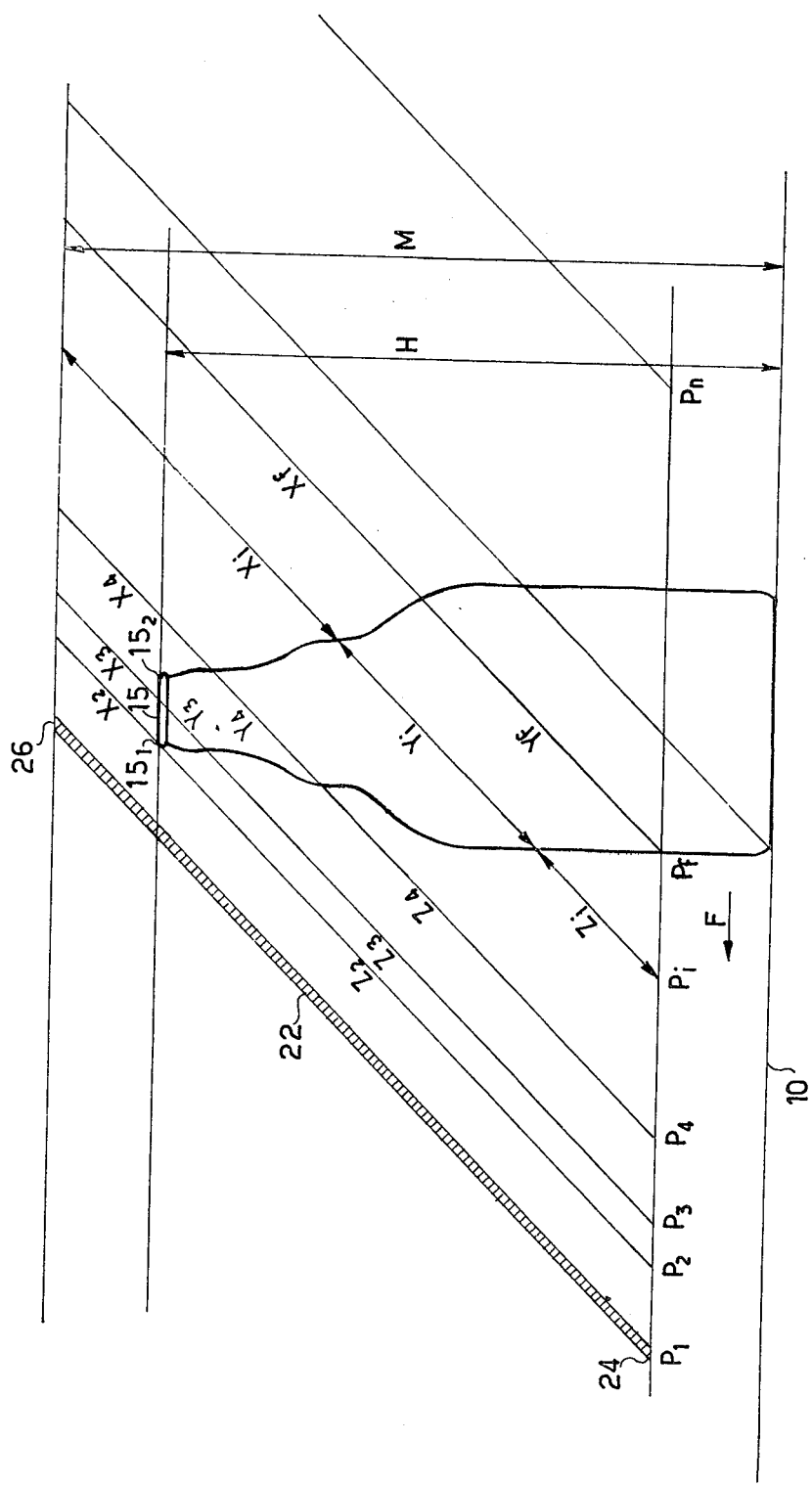
FIG. 2 is a profile view of a bottle and a receiver, for illustrating the various relative positions of said elements.

Such a difficulty is not to be feared with a receiver the end 20 of which is positioned at a distance M of platform 10 as a function of the criteria previously indicated when the bottle to be identified is made to progress in the direction of arrow F, shown in FIG. 2, since a segment X and a segment Z appear at the very moment when said bottle meets the radiation intended for the receiver 22. From this moment, it is possible to constantly follow the values of X and Z, without having to pay some attention to the more or less important quantity of radiation incident on area X, under the condition that one can determine sufficiently clearly the illumination discontinuities corresponding to the transitions between said occluded area Y and the illuminated areas X and Z.

This is the reason why the processing unit is arranged as indicated hereabove for initiating this examination of the illumination levels of the points of receiver 22 by starting from the respective ends of each of segments X and Z, viz. from the ends of said receiver 22.

One should note that even with transparent bottles, the edges of the latter which correspond to the transitions X, Y and Y, Z are quite clear. Indeed, at the edge of the bottle, the thickness of the glass in the direction of the light rays between the source and the receiver is much more important than the same thickness in the central portion of the bottle. The result is a higher source light absorption by the bottle edges than by the central portion of the latter. This phenomenon is illustrated in FIG. 4 where are plotted, in abscissa, the lengths measured along the receiver segment, and in ordinate the illumination levels e of each of the receiver points. The points of segments X and Z are at a uniform level E. The central portion of segment Y also receives an illumination which can be close to E for a rather thin white glass. On the contrary, the illumination of Y in the vicinity of the edges $T_1$ and $T_2$ of the bottle is close to zero. Thus, in position $P'_i$ (FIG. 3), the regions $X_i$ and $Z_i$ may be determined in a perfectly clear fashion.

In order to carry out the read-out of values X and Z, it is preferable to determine the value of Z corresponding to each value of X for obtaining a relation of $Z=F(X)$ between said two parameters, as previously indicated.

Due in particular to the narrow shape of the bottle 12 at its upper portion (FIG. 2), the segment X of receiver 22 one end of which bears against the profile of the bottle as it moves past it has an inclination relative to the perpendicular to said profile at its intersection point with the receiver which is generally smaller than that of segment Z relative to the perpendicular to the profile at the point where it meets segment Z. The result is that the length of segment X increases from the upper edge $15_2$ of bottle 12, in a rather regular way as a function of the advancement of the bottle. The value of the length of X is a function which is substantially uniform of the movement of said bottle.

On the contrary (FIG. 3), if one observes in particular the relative position $P'_R$ of receiver 22 relative to the bottle 83, it appears that with some profile bottles at least, the segment Z can be the object of discontinued variations. Such is the case when the bottle passess in positions where the line of receiver 22 is tangent the bottle profile 83. Thus, for example, when the relative position of the bottle and of the receiver 22 passes from the position marked $P'_r$ to the position marked $P'_{t'}$, there is a position $P'_s$ where the line of receiver 22 is tangent the shoulder 85 of said bottle, and the value of Z is subject to a discontinuity between values $Z_r$ and $Z_t$.

On the other hand, one notes that even when the bottle profile 82 is such that there is no tangential point such as 85, the more pronounced inclination of segment Z on the corresponding profile (left-hand side of the bottle in FIGS. 2 and 3) is the origin of quicker variations of Z as a function of the advancement movement of the bottle (profile in dotted lines in FIG. 3). On the contrary, the end of segment X bearing on the bottle profile moves relatively progressively, in a manner similar to the finger of a probe by following the travelling movement of the bottle with a good precision and without being subjected to abrupt variations or changes of direction, as results from the observation of segments $X_p$ to $X_t$ in FIG. 3.

If advantage is taken of this observation for carrying out the read-out of the values of Z as a function of those of X by determining, for each incremental increase of the value of Z which is measured, the corresponding Z value. Thus is obtained a sequence of discrete values $Z_i$ as a function of a continuous sequence of the $X_i$ values increasing uniformly.

Said values $Z_i$ are stored in positions of the read-out pattern memory 60 the address of which is directly determined as a function of the ranking number of each value $X_i$. Memory 60 includes 256 memory positions and the read-out of a bottle profile is carried out, in the case of the receiver with a network of 256 photodiodes, by regularly filling up a sub-assembly of said positions by starting from the first for value $X_2$ when the edge $15_1$ of the bottle reaches receiver 22.

The processing circuit is programmed to initiate the read-out as soon as the read-out circuit 50 indicates that a first photodiode between ends 24 and 26 of receiver 22 is occluded by the passage of an object on the conveyor. The storage is carried on until the processing circuit 56 receives from said read-out circuit 50 an indication that the length $Z_f$ of the second segment is equal to zero (or has reached a predetermined minimum), said indication corresponding to the position $P_f$ in FIG. 2 where the bottle silhouette meets the lower end 24 of the receiver 22.

From this moment, the acquisition of the measurements is over and the processing unit 56 proceeds to the identification processing as such. To this effect, the reference pattern shape memory 64, which is for instance a REPROM memory or a C-MOS battery memory, contains a series of recordings of relations $Z=F(X)$ in a form similar to that just described with reference to the read-out pattern memory 60 and corresponding each to a determined bottle type for which the return of the deposit is accepted. From preliminary statistical studies bearing on the various typical shapes of the bottles for which a deposit is returned, it has been possible to classify some parameters (height, diameter of the shaft, etc.) as a function of their efficiency as regards the sorting out between the patterns in order to identify a given bottle. The processing unit is arranged for comparing said parameters in the order of their order of decreasing selectivity, with a view to minimizing the identification time.

Figure 6:
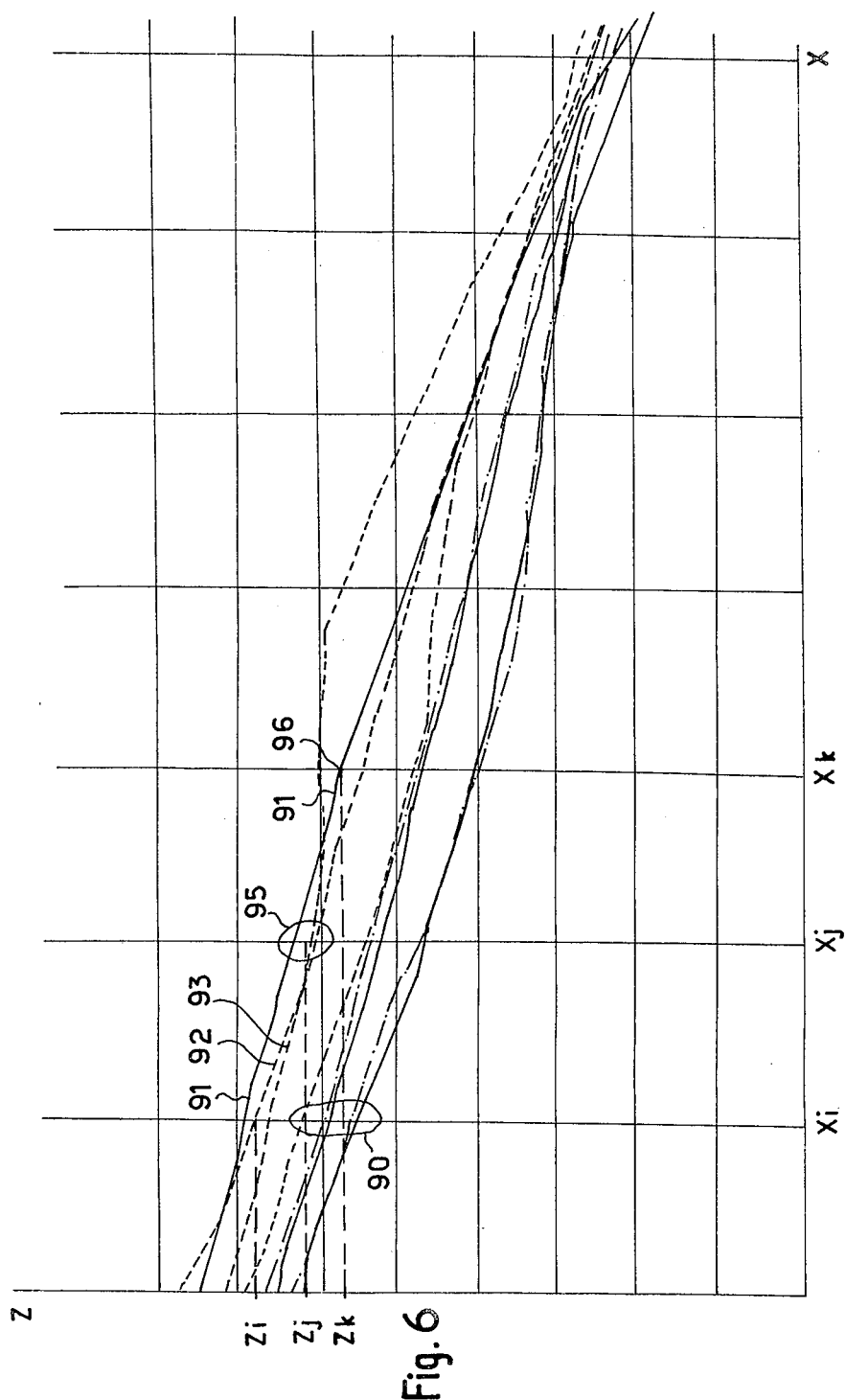
FIG. 6 is a graph of typical curves used for recognizing the shape of the object to be identified.

FIG. 6 shows a series of curves corresponding each to characteristics type or pattern relation of a bottle determined shape. The determination of value $X_2$ allows carrying out a first comparison of said value with all the starting values $X_{2k}$ of the relations corresponding to these different bottle types. So, a first selection allows eliminating all the curves whose starting abscissa $X_{2k}$ does not correspond, within the tolerance limits of the identification procedure, to the value $X_2$ recorded in the read-out pattern memory 60. A large number of remaining patterns are then eliminated by determining the value X corresponding to $Z=0$, said value being indicative of the bottle diameter and by comparing it to the corresponding values ($Z=0$) of the patterns stored in memory 64.

After these preliminary elimination procedures, it is possible to select a number of points characterized by values $X_i$, $X_j$, $X_k$, etc . . . , (FIG. 6) and the corresponding values $Z_i$, $Z_j$, $Z_k$ stored for determining the typical relation to which may be related the relation stored in memory 60, or in the absence of such a relation, for rejecting the bottle.

Thus, for example, the processing circuit 56 queries a position $X_i$ of the read-out pattern memory 60 for extracting a corresponding value $Z_i$; then it queries successively the positions $X_i$ corresponding to the various patterns in memory 64 for carrying out a comparison of the corresponding values $Z_{gi}$ with the value $Z_i$ extracted from memory 60. In the case of FIG. 6, such a comparison process allows eliminating the values $Z_{gi}$ of abscissa $X_i$ surrounded by a circle 90 in the figure, and eliminating the relations shown by the corresponding curves in said figure. Thus, only the three relations 91, 92 and 93 for which the ordinates $Z_{gi}$ are relatively close to $Z_i$ remain under consideration. The processing circuit then queries the memory position 60 $X_j$ for obtaining the value $Z_j$, and memory 64 is again queried in order to extract from it the ordinates $Z_{gi}$ of the three patterns 91, 92 and 93. In the example of FIG. 6, these three values in circle 95 are sufficiently close to each other so as not to allow a reliable selection of one of said patterns; consequently, the processing unit 56 proceeds to the interrogation of the memory position $X_k$ in memory 60 for determining value $Z_k$, and proceeds then to the interrogation of memory positions $X_k$ of the three patterns 91, 92 and 93 in memory 64. This last interrogation, as is shown in FIG. 6, allows selecting without ambiguity the curve 91 as possessing a point 96 of ordinate $Z_{gk}$ very close to $Z_k$ and eliminating by way of consequence the two other pattern curves 92 and 93. One is not satisfied with the concordance read for accepting the pattern 91 as corresponding to the bottle to be identified and one goes on checking the concordance of the values Z which correspond to abscissa X for the read-out of memory 6, and the selected pattern until all the stored values are exhausted, so as to reject the bottle as not returnable if some of the points read out do not correspond to said pattern.

Practically, it has been established that a relatively limited number of points, for example a dozen, was often sufficient for obtaining a good selection or preselection of a pattern amongst various patterns of the bottles to be returned.

Of course, it is possible to use the measurements carried out for improving still more the precision of the identification of the objects passed through the machine, for example by using procedures for recognizing the shapes. In some cases, one can also use the measurements of the illumination level corresponding to the central portion of the occluded region Y and to record them in the memory illumination register for carrying out an extral discrimination between the bottles which can have shapes very similar but which are made of glasses having very different transparency coefficients (tinted glass or white glass for example).

An embodiment of a machine according to the invention (FIG. 7) comprises a disc 101 driven in rotation about its axis 102 by a motor 99. Said disc is mounted horizontally on a frame 103 on one side of which is provided an opening 104 for admitting the bottles on the periphery of disc 101. A sensor 105 detects the presence of a bottle at the inlet 104. A turnstile 106, blocked by an electromagnet 107, stops the bottle temporarily for a time during which another bottle is still in course of identification.

A sensor 108 detects the presence of a bottle in the turnstile 106.

The bottles placed vertically on disc 101 penetrate then a read-out and analysis region 110 comprising, in particular, an elongated fluorescent lamp 112 which is projected in the horizontal plane according to a segment of a straight line substantially tangent the periphery of disc 101 and inclined over about 45° on the plane of said disc. The end 114 of the lamp 112 which is on the inlet side of the bottles is at a higher level than the maximum height of the bottles travelling on disc 101. In a direction (as viewed in a plane) which is diametrically opposite the light source 112 is placed a photodiode network detector 120 comprising a lens 122. This detector is situated substantially above the periphery of disc 101 at a height sufficient for avoiding an interference with the path of travel of the bottles placed on the periphery of the latter. The optical axis 124 of lens 122 is directed towards the middle 125 of lamp 112 in a direction inclined over the horizontal.

The height of the middle 125 of lamp 112 is smaller than the maximum height of the bottles to be analyzed.

The lens 122 forms on the sensitive portion of the detector 120 an image of the elongated source 112. When a bottle passes through space 110, the illumination of said image varies as a function of the interception of a portion of the radiation 129 by the bottle. When the axis 132 of a bottle such as 130 in FIG. 7 reaches the vicinity of the optical axis 124 of the detector, and therefore the middle 125 of the source, the image of the latter on the sensitive portion of the detector comprises three segments, amongst which a central segment occluded by the bottle 130 and flanked by two bright segments corresponding to each end of the source 112. The processing unit 56 controls (FIG. 5) the analysis of said image as previously indicated, and the lengths of the lighted segments are recorded under the control of the processing circuit 56 in the read-out pattern memory 60.

Once the bottle 130 has crossed the region 110, it comes in contact with a mobile deflector 135 controlled by an electromagnet 136. If the identification processing shows that the shape of said bottle corresponds to one of the stored profiles or patterns, the processing circuit causes, through the blockage of electromagnet 136, the deflection of bottle 130 towards the periphery of the disc so as to deviate the latter in the direction of a plunger 138 controlled by a motor 139 as a function of the detection by a sensor 137 and of front and rear limit sensors 133.

If the shape of the bottle 130 has not been identified as corresponding to one of the typical profiles giving right to the return of a deposit, the deflector 135 is freed by the electromagnet 136 and the bottle goes on turning on the periphery of disc 101, passing under detector 120 for reaching a region 140 in the vicinity of opening 104 where it can be taken back by the customer. If it is not taken back, the disc, by going on rotating, pushes it in contact with a deflector 142 which pushes it back radially towards the center of the disc towards an opening 146 in the center of the latter and through which the bottle is discharged.

The processing circuit 56 provides the appropriate sequential operations consisting in starting the disc 10, the lamp 112, the detector 120, the coordination of the turnstile operations 106, of the acquisition of the measurements and the recognition of the bottles, of the deflector 135 and the plunger 38 as a function of the indications from sensors 105, 108, 133 and 137. Particularly, it exploits the results of the recognition for the control of plunger 138 and of the refusal control light 76, as well as of the printer 74 for delivering a printed ticket comprising, for each customer, the number and type of bottles brought back and the corrresponding price.

According to an alternative, an identification machine of the type just described is applied to the constitution of a bottle sorting machine adapted for operating at a high speed in bottling plants or wholesale warehouses. The sorting machine is equipped with a plurality of plungers distributed along the path of travel of the bottles when they come out from the radiation. Each plunger is mounted opposite a respective conveying path opening into an accumulation table for the bottles discharged in said path by the respective plunger. The plungers are associated with electromagnets controlled by the processing circuit so as to carry out the selection of the bottles towards the various conveyor paths as a function of their dimensions and shapes as detected during the identification phase.

According to another alternative, instead of the photodiode bar of FIG. 1, one may use for the receiver 22 a surface photodetector such as the sensitive surface of a television camera (VIDICON tube), associated with means adapted for detecting, during the scanning, the illumination of a useful segment of said detecting surface along which is formed an image of the fluorescent tube presenting a segment occluded by the bottle. The analysis of said image may be carried out by the scanning under the control of the processing unit by detecting the position in time of signals corresponding to the illuminated points.

I claim:

1. An identification method for objects, in which each object is made to travel between a radiation source and a receiver having a useful portion, responsive to the radiation, elongated in a direction oblique relative to the travelling direction of the cast shadow of the object on said receiver, wherein, during the travelling, there exists a segment of the receiver which is at least partly occluded by the object, and first and second segments not occluded on either side of said occluded segment, and wherein one reads out corresponding length variations of at least two of said three segments for obtaining a characteristic relation of the object shape.

2. A method according to claim 1, wherein said characteristic relation is compared with preestablished relations corresponding to a set of predetermined objects for deducing therefrom the shape of the object.

3. A method according to claim 1, wherein the objects posssess an axis of symmetry in the vertical direction and travel perpendicularly to said direction.

4. A method according to claim 1, wherein one notes the corresponding length variations of the first and of the second segment.

5. A method according to claim 4, wherein said elongated receiver, taking in account the maximum dimension of the objects to be identified, is placed in a position such that one of its ends is never occluded by the objects belonging to a predetermined set.

6. A method according to claim 5, wherein said objects are made to travel relative to said receiver in a direction such that during the travelling, the object penetrates the radiation incident on the receiver by occluding a region situated between the ends of the latter, so as to supply values of the length of the first and second segments which are not zero from the very beginning of the passage of the object between the source and the receiver.

7. A method according to claim 6, wherein the lengths of the first and second segments are determined by examining the radiation level received by each of said segments, from the respective end of the elongated receiver and in the direction of the other end, until a point of said receiver which receives a radiation level corresponding to an occlusion by an edge of the object is met.

8. A method according to claim 6 in which the receiver is made of discrete elements, wherein the length of each segment is determined by counting the number of discrete elements receiving rays from the source which are not intercepted by the object, by starting from the respective end of the receiver for each of said first and second segments.

9. A method according to claim 8 in which the objects are bottles or similar objects having a narrow shape in a direction transverse relative to the travelling direction so that, during the travelling, the inclination of the first segment of the receiver relative to the perpendicular to the corresponding side of said narrowed profile is less than that of the second segment relative to the perpendicular to the corresponding side of the object profile, wherein the length variation of the second segment is determined as a function of that of the first segment.

10. A method according to claim 9, wherein the length variations of the first segment are measured in quantified values and the length values of the second segment corresponding to length increments of the first segment are read out.

11. A method according to claim 10, wherein measured respective values of the length of the second segment are recorded in memory positions corresponding to a sequence of values of the length of the first segment.

12. A machine for the identification of objects, of the type comprising a conveyor, a receiver responsive to radiation adapted to be intercepted by objects (12) travelling on said conveyor and casting a shadow on said receiver, wherein said receiver is obliquely elongated relative to the travelling direction of said shadow on the receiver so that there exists, during the travelling of each object, a segment of said receiver the points of which are at least partly occluded by the object and first and second segments not occluded by the object on either side of said occluded segment, the machine further comprising means for reading out the length of at least two of said three segments for a plurality of positions of each object relative to said receiver.

13. A machine according to claim 12, wherein the readout means comprise recording means of the length of the second segment in memory positions the address of which correspond to the respective values of the length of the first segment.

14. A machine according to claim 13, characterized in that it comprises further an oblique elongated radiation source on the other side of the receiver relative to a space in which the objects travel and optical means for forming an image of said source on the receiver.

15. A machine according to claim 14, wherein said receiver is constituted by a photodiode bar.

16. A machine according to claim 14, wherein the receiver comprises a surface detector associated with means for detecting the illumination of a rectilinear segment of said oblique detector relative to the travelling direction on said detector of the cast shadow of the objects carried by the conveyor.

17. A machine according to claim 15, wherein the elongated receiver is placed, taking in account the maximum dimension of the objects to be identified in a predetermined set, in a manner such that one of its ends is never occluded by said objects.

18. A machine according to claim 17, wherein the travelling direction of the conveyor is adapted for permitting the occlusion of an intermediate region of the receiver for each object at the moment when said object penetrates the radiation incident on the receiver.

19. A machine according to claim 18, wherein the read-out means comprise means for examining the first and second segments by starting from the corresponding end of the receiver towards the opposite end, and threshold detection means for detecting illumination transitions between a non occluded segment and an occluded segment.

20. A machine according to claim 19, characterized in that it possesses also means for reading out the existence of weakly occluded portions by a transparent object, of the intermediate segment between the first and second segments.

21. A machine according to claim 20 for the return of deposits on bottles, wherein said conveyor comprises a horizontal platform on which said bottles can be placed, with their axis vertical.

22. A machine according to claim 21, wherein the conveyor is a horizontal transporting means for bottles, with a looped path of travel, and the receiver is placed at a level higher than the height of the tallest bottle accepted in the machine.

23. A machine according to claim 20 wherein said conveyor comprises a disc horizontally mounted on frame means for rotation about its axis.

24. A machine according to claim 23, wherein said frame means includes a first opening for admitting objects onto the periphery of said conveyor.

25. A machine according to claim 24, wherein said conveyor possesses a second centrally disposed opening for the discharge of objects, to waste.

26. A machine according to claim 25, wherein deflector means are provided responsive to signals from said receiver, to deflect objects on said conveyor to either said first or said second opening.

27. A machine according to claim 24 including first sensor means adapted to detect the presence of an object at said first opening; gate means for temporarily restricting movement of an object at said first opening; and second sensor means adapted to detect the presence of an object in said gate means.

* * * * *